US005756845A

United States Patent [19]
Voit et al.

[11] Patent Number: 5,756,845
[45] Date of Patent: May 26, 1998

[54] PREPARATION OF 3-AMINOMETHYL-3,5,5-TRIMETHYLCYCLOHEXYLAMINE

[75] Inventors: Guido Voit, Schriesheim; Tom Witzel, Ludwigshafen; Boris Breitscheidel, Fulda; Wolfgang Harder, Weinheim; Hermann Luyken, Ludwigshafen; Axel Paul, Lampertheim; Karl-Heinz Ross, Grünstadt; Peter Wahl, Ladenburg, all of Germany

[73] Assignee: BASF Aktiengesellschaft, Ludwigshafen, Germany

[21] Appl. No.: 608,485

[22] Filed: Feb. 28, 1996

[30] Foreign Application Priority Data

Mar. 3, 1995 [DE] Germany ............... 195 07 398.3

[51] Int. Cl.⁶ .................................................. C07C 209/48
[52] U.S. Cl. .................................................. 564/448; 564/446
[58] Field of Search ............................................ 564/446, 448

[56] References Cited

U.S. PATENT DOCUMENTS 5,371,292  12/1994  Merger et al. .
5,583,260  12/1996  Haas et al. ................... 564/446

FOREIGN PATENT DOCUMENTS 0 449 089  3/1991  European Pat. Off. .
A-503 246  9/1992  European Pat. Off. .
A-534 449  3/1993  European Pat. Off. .
A-636 409  2/1995  European Pat. Off. .
A-659 733  6/1995  European Pat. Off. .

Primary Examiner—Brian M. Burn
Attorney, Agent, or Firm—John H. Shurtleff

[57] ABSTRACT

A process for the preparation of 3-aminomethyl-3,5,5-trimethylcyclohexylamine from 3-cyano-3,5,5-trimethylcyclohexanone which requires three spatially separated reaction spaces, in order to carry out the following three steps in sequence:

a) reacting the 3-cyano-3,5,5-trimethylcyclohexanone with excess ammonia on acidic metal-oxide catalysts in a first reaction space at from 20° to 150° C. and from 50 to 300 bar, b) hydrogenating the resultant reaction products using hydrogen in a second reaction space in the presence of excess ammonia and preferably liquid ammonia on hydrogenation catalysts, optionally using basic components or on neutral or basic supports at from 50° to 100° C. and at from 50 to 300 bar, and c) hydrogenating the resultant reaction products in the presence of hydrogen and also ammonia in a third reaction space on hydrogenation catalysts, optionally using basic components or on neutral or basic supports at from 110° to 160° C. and at from 150 to 300 bar.

These three steps in sequence provide a substantially complete reaction of the original 3-cyano-3,3,5-trimethylcyclohexanone reactant with a yield of 96% of the desired diamino product in which the cis-content of the diamine is 70%.

10 Claims, No Drawings

PREPARATION OF 3-AMINOMETHYL-3,5,5-TRIMETHYLCYCLOHEXYLAMINE

The present invention relates to a process for the preparation of 3-aminomethyl-3,5,5-trimethylcyclohexylamine (isophoronediamine, IPDA) by reacting 3-cyano-3,5,5-trimethylcyclohexanone (isophorone nitrile, IPN) with ammonia and hydrogen in three spatially separated reaction spaces.

EP-A-449 089 discloses a process for the preparation of IPDA from IPN in which, in a first step, IPN is reacted with ammonia on acidic metal oxides to give isophorone nitrile imine, and this is hydrogenated, in a second step, in the presence of hydrogen on known hydrogenation metals, preferably cobalt and/or ruthenium, on basic supports or in the presence of basic components, such as alkali or alkaline earth metal hydroxides, to give IPDA. The IPDA is produced in two stereoisomeric forms in which the amino function in the 1-position and the aminomethyl function in the 3-position are in the cis or trans position relative to one another (cis-IPDA and trans-IPDA).

IPDA is used, for example, as an epoxy resin curing agent or - via isophorone diisocyanate - as a component of polyurethane. There are specific applications in which the cis/trans isomer ratio is important, a cis content of, for example, >67% frequently being desired.

The process described in EP-A-449 089 enables the preparation of IPDA from IPN with - compared with the previously described processes - a high space-time yield and a high chemical yield. For example, use of aluminum oxide or titanium dioxide in the imination and highly active cobalt catalysts for the hydrogenation, as described, for example, in DE-A-43 258 847, gives IPDA yields of up to 98%, but the cis content here is only 60%. An increase in the cis content to, for example, 68% is possible, but only with a drop in yield.

It is an object of the present invention to provide an improved process which enables both a high space-time yield and high chemical yield and an increased proportion of cis-IPDA.

We have found that this object is achieved by a novel and improved process for the preparation of 3-aminomethyl-3,5,5-trimethylcyclohexylamine from 3-cyano-3,5,5-trimethylcyclohexanone in three spatially separated reaction spaces, which comprises a) reacting the 3-cyano-3,5,5-trimethylcyclohexanone with excess ammonia on acidic metal-oxide catalysts in a first reaction space at from 20° to 150° C. and from 50 to 300 bar, b) hydrogenating the resultant reaction products using hydrogen in a second reaction space in the presence of excess ammonia on hydrogenation catalysts, with or without basic components or on neutral or basic supports at from 50° to 100° C. and at from 50 to 300 bar, and c) hydrogenating the resultant reaction products in the presence of hydrogen in a third reaction space on hydrogenation catalysts, with or without basic components or on neutral or basic supports at from 110° to 160° C. and at from 150 to 300 bar.

The novel process can be carried out as follows:

a) In a first step, 3-cyano-3,5,5-trimethylcyclohexanone is reacted with excess ammonia at from 20° to 150° C., preferably at from 30° to 130° C., particularly preferably at from 50° to 100° C., and at from 50 to 300 bar, preferably at from 100 to 250 bar, to give 3-cyano-3,5,5-trimethylcyclohexanoneimine.

Suitable acidic metal-oxide catalysts are aluminum oxide, silicon dioxide, titanium dioxide and zirconium dioxide, preferably aluminum oxide, titanium dioxide and zirconium dioxide, in particular aluminum oxide and titanium dioxide.

During the imination, a weight hourly space velocity of from 0.01 to 10 kg, preferably from 0.05 to 7 kg, particularly preferably from 0.1 to 5 kg, of 3-cyano-3,5,5-trimethylcyclohexanone per kg of catalyst and per hour is maintained. It is expedient, but not absolutely necessary, to employ from 5 to 500 mol, preferably from 10 to 400 mol, particularly preferably from 20 to 300 mol, of $NH_3$ per mole of 3-cyano-3,5,5-trimethylcyclohexanone in the imination. The imination of 3-cyano-3,5,5-trimethylcyclohexanone can also be carried out in the presence of a solvent, for example alkanols or tetrahydrofuran, but is preferably carried out without addition of a solvent.

The imination is preferably carried out continuously, for example in pressure vessels or pressure vessel cascades. In a particularly preferred embodiment, 3-cyano-3,5,5-trimethyl-cyclohexanone and $NH_3$ are passed through a tubular reactor containing the imination catalyst in the form of a fixed bed.

b) The product obtained in this way is subjected, in a second step, to catalytic hydrogenation using from 3 to 10,000 mole-equivalents, preferably from 4.5 to 100 mole-equivalents, of hydrogen, if desired after introduction of further ammonia.

During the hydrogenation, the temperature is held at from 60° to 100° C. and the pressure is held at from 50 to 300 bar, preferably from 100 to 250 bar.

The weight hourly space velocity is expediently in the range from 0.01 to 5 kg/[kg.h], preferably from 0.02 to 2.5 kg/[kg.h], particularly preferably from 0.05 to 2 kg/[kg.h].

The hydrogenation is preferably carried out in liquid ammonia. From 5 to 500 mol, preferably from 10 to 400 mol, particularly preferably from 20 to 300 mol, of $NH_3$ are employed per mole of 3-cyano-3,5,5-trimethylcyclohexanoneimine. The $NH_3$ available is expediently at least the amount present after the prior preparation of 3-cyano-3,5,5-trimethylcyclohexanoneimine from the corresponding 3-cyano-3,5,5-trimethylcyclohexanone. However, the $NH_3$ content can also be increased to the desired level before the hydrogenation by introduction of additional $NH_3$.

The reductive amination of 3-cyano-3,5,5-trimethylcyclohexanoneimine is preferably carried out continuously, for example in pressure-tight stirred vessels or in a stirred vessel cascade. In a particularly preferred embodiment, tubular reactors are employed in which the product mixture from the imination is passed upward or downward over a fixed catalyst bed.

The reactor product contains components which have still not reacted completely, for example the aminonitrile, which is extremely difficult to separate from IPDA by distillation.

c) The reaction product from b) is hydrogenated, in a third step, in the presence of hydrogen and ammonia at from 110° to 160° C. and at from 50 to 300 bar, preferably at from 100 to 250 bar. The amounts of ammonia and hydrogen available are expediently those present in the product leaving the reactor after step b).

The reactor in step c) can be significantly smaller than the reactor in step b).

After the hydrogenation, any excess ammonia is removed under pressure. The resultant 3-aminomethyl-3,5,5-trimethylcyclohexylamine can be isolated by fractional distillation.

In principle, the hydrogenation can be carried out in the presence of any common hydrogenation catalyst containing nickel, cobalt, iron, copper, ruthenium or another noble metal from subgroup VIII of the Periodic Table. Preference is given to ruthenium, cobalt and nickel catalysts. Particular preference is given to ruthenium and cobalt catalysts. The catalytically active metals can be unsupported or supported.

Examples of supports which can be used are aluminum oxide, titanium dioxide, zirconium dioxide, zinc oxide and magnesium oxide/aluminum oxide; preference is given to supports containing basic components, such as oxides and hydroxides of alkali and alkaline earth metals. Particular preference is given to unsupported catalysts, as disclosed, for example, in DE-A-43 25 847, which contain basic components, such as oxides or hydroxides of alkali and alkaline earth metals. The basic component can, if desired, also be introduced during the hydrogenation process, for example as a solution of alkali metal hydroxides or alkaline earth metal hydroxides in water.

EXAMPLES

Example 1

The apparatus comprised three reactors connected in series. The first reactor was filled with 240 l of gamma-aluminum oxide pellets (4 mm), the second reactor was filled with 600 l of a reduced cobalt catalyst (90% cobalt with 5% manganese and 1.9% sodium) in the form of 4 mm pellets, and the third reactor was filled with 200 l of a reduced cobalt catalyst (90% cobalt with 5% manganese and 1.9% sodium) in the form of 4 mm pellets.

At a pressure of 250 bar, 160 l/h of IPN and 760 l/h of ammonia were pumped into the first reactor. 250 l/h of ammonia and 250 ml/h of 2% aqueous sodium hydroxide solution and 220 m$^3$ (s.t.p.)/h of hydrogen were introduced before the second reactor. After the second reactor, the majority of the hydrogen was removed in a high-pressure separator and recycled, and, after addition of 50 m$^3$ (s.t.p.) of hydrogen, the liquid phase was pumped through the third reactor. The temperatures were 90° C. in the imination reactor, 75° C. (inlet temperature) to 100° C. (outlet temperature) in the first hydrogenation reactor and 140° C. in the second hydrogenation reactor. After the second hydrogenation reactor, the reaction mixture, after removal of ammonia, contained 96% of IPDA and 1.3% of azabicyclooctane according to analysis by gas chromatography (without water). The aminonitrile content was less than 200 ppm, and the content of cis-IPDA was 70%. After the first reactor, further unsaturated components, besides 3.5% of aminonitrile, were present in an amount of from 3 to 6%.

Comparative Example A: (as in EP-A-449 089, Example 4)

The apparatus comprised two reactors: the first reactor was filled with 170 l of gamma-aluminum oxide pellets (4 mm), and the second reactor was filled with 330 l of a reduced cobalt catalyst (90% cobalt with 5% manganese and 1.9% sodium) in the form of 4 mm pellets.

At a pressure of 250 bar, 72 l/h of IPN and 630 l/h of ammonia were pumped into the two reactors connected in series. In addition, 250 ml/h of 2% aqueous sodium hydroxide solution and 150 m$^3$ (s.t.p.)/h of hydrogen were introduced into the hydrogenation reactor. The temperature in the imination reactor was 90° C., the hydrogenation reactor inlet temperature was 115° C. and the hydrogenation reactor outlet temperature was 140° C. The hydrogenation product contained, in addition to ammonia and water, 97% of IPDA, 1% of 1,3,3-trimethyl-6-azabicyclo[3.2.1]octane and <200 ppm of aminonitrile according to analysis by gas chromatography. The cis content in the IPDA was 60%.

If only 150 ml/h of 2% sodium hydroxide solution were introduced, the IPDA content dropped to 92.4%, the content of 1,3,3-trimethyl-6-azabicyclooctane increased to 4.5% and the cis-IPDA content rose to 68%.

If the hydrogenation temperature was reduced, the aminonitrile content in both cases rose to values of >1000 ppm.

We claim:

1. A process for the preparation of 3-aminomethyl-3,5,5-trimethylcyclohexylamine from 3-cyano-3,5,5-trimethylcyclohexanone in three spatially separated reaction spaces, which comprises three sequential steps:

a) reacting the 3-cyano-3,5,5-trimethylcyclohexanone with excess ammonia on acidic metal-oxide catalysts in a first reaction space at from 20° to 150° C. and from 50 to 300 bar, b) hydrogenating the resultant reaction products using hydrogen in a second reaction space in the presence of excess ammonia on hydrogenation catalysts, with or without basic components or on neutral or basic supports at from 50° to 100° C. and at from 50 to 300 bar, and c) hydrogenating the resultant reaction products in the presence of hydrogen and ammonia in a third reaction space on hydrogenation catalysts, with or without basic components or on neutral or basic supports at from 110° to 160° C. and at from 150 to 300 bar.

2. A process for the preparation of 3-aminomethyl-3,5,5-trimethylcyclohexylamine as claimed in claim 1, wherein the hydrogenation catalysts employed contain cobalt, nickel, ruthenium and/or other noble metals.

3. A process for the preparation of 3-aminomethyl-3,5,5-trimethylcyclohexylamine as claimed in claim 1, wherein the basic components in the hydrogenation catalysts are oxides or hydroxides of alkali metals or alkaline earth metals.

4. A process as claimed in claim 1, wherein the hydrogenation catalyst is selected from the group consisting of manganese, iron, nickel, cobalt, copper and a noble metal of subgroup VII of the Periodic Table or mixtures thereof.

5. A process as claimed in claim 1, wherein the hydrogenation catalyst is selected from the group consisting of cobalt, nickel, manganese and ruthenium, including mixtures thereof.

6. A process as claimed in claim 1, wherein the hydrogenation catalyst is an unsupported metal selected from the group consisting of manganese, cobalt, nickel, copper, ruthenium and mixtures thereof.

7. A process as claimed in claim 6, wherein the hydrogenation steps (b) and (c) are carried out in the presence of a basic component.

8. A process as claimed in claim 7, wherein the basic component is added as an alkali metal or alkaline earth metal oxide or hydroxide as a basic component of the catalyst or as the hydroxide dissolved in water.

9. A process as claimed in claim 1, wherein the imination of the first step (a) is carried out at a temperature of from 30° to 130° C. and under a pressure of from 100 to 250 bar, the hydrogenation of the second step is carried out at a temperature of from 60° to 100° C. and under pressure of from 100 to 250 bar, and the hydrogenation in the third step (c) is carried out under a pressure of from 100 to 250 bar.

10. A process as claimed in claim 1, wherein the hydrogenation step (b) is carried out in liquid ammonia.

* * * * *